(12) United States Patent
Brierton et al.

(10) Patent No.: US 12,179,466 B2
(45) Date of Patent: Dec. 31, 2024

(54) SYSTEM AND METHOD FOR THE AUTOMATED OPENING OF A STERILE TUBING WELD

(71) Applicant: Fenwal, Inc., Lake Zurich, IL (US)

(72) Inventors: Mark Joseph Brierton, Cary, IL (US); James Knapp, Round Lake, IL (US); Michael Platt, Prospect Heights, IL (US)

(73) Assignee: Fenwal, Inc., Lake Zurich, IL (US)

( * ) Notice: Subject to any disclaimer, the term of this patent is extended or adjusted under 35 U.S.C. 154(b) by 62 days.

(21) Appl. No.: 17/410,996

(22) Filed: Aug. 24, 2021

(65) Prior Publication Data

US 2022/0065365 A1 Mar. 3, 2022

Related U.S. Application Data

(60) Provisional application No. 63/069,801, filed on Aug. 25, 2020.

(51) Int. Cl.
*B32B 43/00* (2006.01)
*A61M 39/10* (2006.01)
*F16L 13/02* (2006.01)

(52) U.S. Cl.
CPC .......... *B32B 43/006* (2013.01); *A61M 39/10* (2013.01); *B32B 2535/00* (2013.01); *F16L 13/02* (2013.01);
(Continued)

(58) Field of Classification Search
CPC ...... A61M 39/10; A61M 39/14; A61M 39/18; B32B 43/006; B32B 2535/00;
(Continued)

(56) References Cited

U.S. PATENT DOCUMENTS

| 4,157,723 | A | 6/1979 | Granzow et al. |
| 4,610,670 | A | 9/1986 | Spencer |

(Continued)

FOREIGN PATENT DOCUMENTS

| EP | 0208004 B1 | 8/1988 |
| EP | 0134630 81 | 5/1989 |

(Continued)

OTHER PUBLICATIONS

"Gongyi Forui Machinery Factory, Double Roller Crusher, Copyright 2012 but attached Youtube Video is dated to Oct. 26, 2018" (Year: 2018).*

(Continued)

*Primary Examiner* — Alex B Efta
*Assistant Examiner* — Alexander S Wright
(74) *Attorney, Agent, or Firm* — Cook Alex Ltd.

(57) ABSTRACT

A system and method for automatically opening a heat bonded connection site between two conjoined tubing segments of a medical fluid path is provided. A pair of rollers is utilized to draw the connection site of the conjoined tubing segments between the rollers to compress the connection site with sufficient force to open the connection site. A guide in the form of an elongated groove is provided in a support surface of the system that properly aligns the seal line axis of the conjoined tubing segments relative to the rollers.

18 Claims, 8 Drawing Sheets

(52) U.S. Cl.
CPC ...... *F16L 2201/44* (2013.01); *Y10T 156/1174* (2015.01); *Y10T 156/1956* (2015.01)

(58) Field of Classification Search
CPC . F16L 13/02; F16L 2201/44; Y10T 156/1174; Y10T 156/1956
See application file for complete search history.

(56) References Cited

U.S. PATENT DOCUMENTS

| | | |
|---|---|---|
| 4,619,642 A | 10/1986 | Spencer |
| 4,737,214 A | 4/1988 | Leurink et al. |
| 4,753,697 A | 6/1988 | Shaposka et al. |
| 5,156,701 A | 10/1992 | Spencer et al. |
| 5,158,630 A | 10/1992 | Shaposka et al. |
| 5,221,267 A | 6/1993 | Folden |
| 5,250,041 A | 10/1993 | Folden et al. |
| 5,256,229 A | 10/1993 | Spencer |
| 5,270,003 A | 12/1993 | Bernes et al. |
| 5,272,304 A | 12/1993 | Been et al. |
| 5,279,685 A | 1/1994 | Ivansons et al. |
| 5,674,333 A | 10/1997 | Spencer |
| 5,836,619 A | 11/1998 | Shemesh et al. |
| 6,026,882 A | 2/2000 | Yamada et al. |
| 6,041,709 A * | 3/2000 | Wells ............... B41F 31/08 417/477.3 |
| 6,322,551 B1 | 11/2001 | Brugger |
| 6,485,593 B1 | 11/2002 | Christoffersen |
| 7,070,589 B2 | 7/2006 | Lolachi et al. |
| 7,766,394 B2 | 8/2010 | Sage et al. |
| 8,146,642 B2 | 4/2012 | Landherr et al. |
| 9,533,135 B2 | 1/2017 | Kusters et al. |
| 10,040,247 B2 | 8/2018 | Schwalm et al. |
| 2003/0141009 A1* | 7/2003 | Landherr .......... B29C 66/82263 156/380.7 |
| 2007/0182055 A1 | 8/2007 | Eells et al. |
| 2007/0296890 A1 | 12/2007 | Mizushima et al. |
| 2011/0144581 A1 | 6/2011 | Irwin et al. |
| 2012/0226229 A1 | 9/2012 | Watanabe et al. |
| 2013/0153048 A1 | 6/2013 | Schwalm et al. |
| 2016/0361531 A1 | 12/2016 | Kusters et al. |

FOREIGN PATENT DOCUMENTS

| | | |
|---|---|---|
| EP | 0194873 B1 | 7/1991 |
| EP | 0507321 | 10/1992 |
| EP | 0515811 A2 | 12/1992 |
| EP | 0723851 A2 | 7/1996 |
| EP | 0728274 A1 | 8/1996 |
| EP | 0847847 A1 | 6/1998 |
| EP | 0599057 B1 | 12/1999 |
| EP | 0623032 B1 | 8/2001 |
| EP | 1066853 B1 | 9/2004 |
| EP | 1108444 B1 | 4/2014 |
| EP | 2957402 A1 | 12/2015 |
| EP | 2089094 B1 | 1/2016 |
| JP | H09206383 | 8/1997 |
| JP | H11178891 A | 7/1999 |
| WO | 1994/012224 | 6/1994 |
| WO | 99/64837 A1 | 12/1999 |
| WO | 03/041746 A2 | 5/2003 |
| WO | 2008/054699 | 5/2008 |
| WO | 2011/144561 | 11/2011 |
| WO | 2011144561 A1 | 11/2011 |
| WO | 2012/022635 | 2/2012 |
| WO | 2013/004322 | 1/2013 |

OTHER PUBLICATIONS

European Patent Office, European Search Report, counterpart EP18167652, dated Aug. 9, 2018 with computer generated English translation.

\* cited by examiner

SYSTEM AND METHOD FOR THE AUTOMATED OPENING OF A STERILE TUBING WELD

RELATED APPLICATIONS

This application claims the benefit of and priority to U.S. Provisional Patent Application Ser. No. 63/069,801, filed Aug. 25, 2020, the contents of which are incorporated by reference herein.

BACKGROUND

The present disclosure generally relates to apparatuses and methods for opening a connection site between two flexible thermoplastic conduits, such as, for example, a sterile connection site in fluid flow tubing in a medical fluid flow circuit employed in collecting, processing, or treating medical fluid such as blood or blood components.

It is well known in the medical industry in general and particularly in the blood banking field to use connection systems for connecting two separate tubing segments of a fluid flow set or circuit in a manner that prevents the introduction of contaminants or preserves the sterility of the tubing, if pre-sterilized, during the connection process. Such systems have found application both in the large scale assembly or manufacture of fluid flow circuits and in the hands of the ultimate user for on-site assembly of fluid flow circuits having a desired configuration. For example, a user may desire to carry out a particular medical procedure, such as for collecting, processing, or treating blood and blood components. These connection devices or systems are commonly referred to in the medical field as sterile connection or sterile docking devices.

Known connection devices or systems include electron beam systems; radiant energy systems that melt facing membranes of fluid flow conduits, as in U.S. Pat. No. 4,157,723; and heated wafer systems that cut and heat tubing segments that are bonded or spliced together, while the ends remain at a molten or semi-molten elevated temperature, such as in U.S. Pat. Nos. 4,753,697, 5,158,630, 5,156,701 and 5,279,685. The disclosures of all of these patents are hereby incorporated herein by reference.

More recently, a novel rotary connection system and apparatus has been described that connects flexible thermoplastic tubing segments by heat or melt bonding the ends together while the ends are individually clamped into a closed position, preventing ambient contamination. Such a system is described in detail in U.S. Pat. No. 10,040,247, which is incorporated by reference herein in its entirety.

The connection made by heated wafer systems as well as by the wafer-free apparatus described above may have a temporary closed condition or crimped shape due to the high temperature and clamping of the tubing segment ends during connection. More specifically, as a result of the particular connection process, a portion of thermoplastic material from the tubing, also referred to as a "skin", "membrane" or "web," may close or reduce the size of the lumen between the tubing segments. In other words, after the connection is made, the tubular segments remain crimped or stuck together at the connection site, and the cross section of the tubular segments is reduced or flattened along a seal line between the tubing segments. This thermoplastic blocking portion of the connection can be broken or otherwise disrupted to open the lumen for fluid flow between the tubing segments by light external pressure or manipulation, including manual or mechanical manipulation, at the connection point or site. Examples of mechanical manipulation may be found in, for example, U.S. Pat. Nos. 4,610,670; 4,619,642; and 5,674,333; EP No. 0599057 B1; and WO 2011144561 A1. U.S. Pat. No. 9,533,135 shows the use of gas pressure or vacuum to open a connection site. The disclosures of all of these patent documents are hereby incorporated herein by reference.

The subject matter of this description relates to an apparatus and method that uses rotatable rollers, to automatically break or otherwise disrupt the thermoplastic skin or web and therefore more fully open such a connection site and the lumen of the tubing segments to allow or improve fluid flow between the connected tubing segments.

SUMMARY

In a first aspect, a system is provided for automatically opening a heat bonded connection site between two conjoined tubing segments of a medical fluid path using rollers in which the conjoined tubing segments define a longitudinal axis and the connection site defines a seal line axis generally perpendicular to the longitudinal axis of the conjoined tubing segments. The system comprises: a support surface having a first axis for receiving the conjoined tubing segments with the longitudinal axis of the conjoined tubing segments in alignment with the first axis of the support surface; first and second spaced-apart rollers, each rotatable about an axis generally perpendicular to the first axis of the support, the first roller being positioned substantially on a first side of the support surface and the second roller being positioned substantially to a second side of the support surface opposite the first side so that the conjoined tubing segments are positioned between the first and second rollers when the conjoined tubing segments are positioned on the support surface with the longitudinal axis in alignment with the first axis, at least one of the first and second rollers being movable toward and away from the other of the first and second rollers; and a drive motor associated with at least one of the first and second rollers for rotating the roller about its axis.

In a second aspect, at least one of the rollers has a concave surface.

In a third aspect, at least one of the rollers has a textured surface.

In a fourth aspect, the support surface has an elongated groove in alignment with the longitudinal axis of the support surface configured to receive the conjoined tubing segments.

In a fifth aspect, the textured surface comprises a series of ridges formed on the surface of the roller, the ridges extending in a direction generally parallel to the axis of rotation of the roller.

In a sixth aspect, the system further comprises a programmable controller for automatically operating the system to: space the first and second rollers apart a distance sufficient to receive the conjoined tubing segments therebetween, to bring the first and second rollers into engagement with the conjoined tubing segments, to rotate the rollers to draw the connection site of the tubing segments therebetween, and to exert a compressive force on the connection site sufficient to open the connection site.

In a seventh aspect, a method is provided for opening a heat-bonded connection site between two conjoined tubing segments of a medical fluid path, the conjoined tubing segments defining a longitudinal axis and the connection site defining a seal line axis generally perpendicular to the longitudinal axis of the conjoined tubing segments. The method comprises: spacing first and second rollers apart a distance sufficient to receive the conjoined tubing segments therebetween; positioning the conjoined tubing segments on a support surface between the first and second rollers with the longitudinal axis of the conjoined tubing segments in alignment with a first axis of the support surface; bringing the first and second rollers into contact with the conjoined tubing segments; rotating the rollers to draw the connection site of the conjoined tubing segments between the rollers so as to exert a pressure on the connection site sufficient to open a flow path between the conjoined tubing segments; stopping rotation of the rollers; and moving the rollers apart a distance sufficient to permit removal of the conjoined tubing segments from between the rollers.

BRIEF DESCRIPTION OF DRAWINGS

Various aspects and features of the present subject matter are seen in the attached drawings, of which:

FIG. 2A is referred to as a top view and the viewing angle is generally parallel to the connection site seal line formed by the crimping action of the sealing or welding apparatus. The viewing angle of FIG. 2B is generally orthogonal to that of FIG. 2A. FIG. 2B is referred to as a side view and is generally perpendicular to the connection site seal line formed by the crimping action of the connection sealing or welding apparatus.

DETAILED DESCRIPTION

Turning now to a more detailed description, the attached drawings are provided for purposes of illustration and not limitation. As noted earlier, the present subject matter is particularly useful in opening a heat or melt bonded or welded connection site formed by connection devices such as, but not limited to that illustrated in U.S. Pat. No. 10,040,247.

Figure 1A:
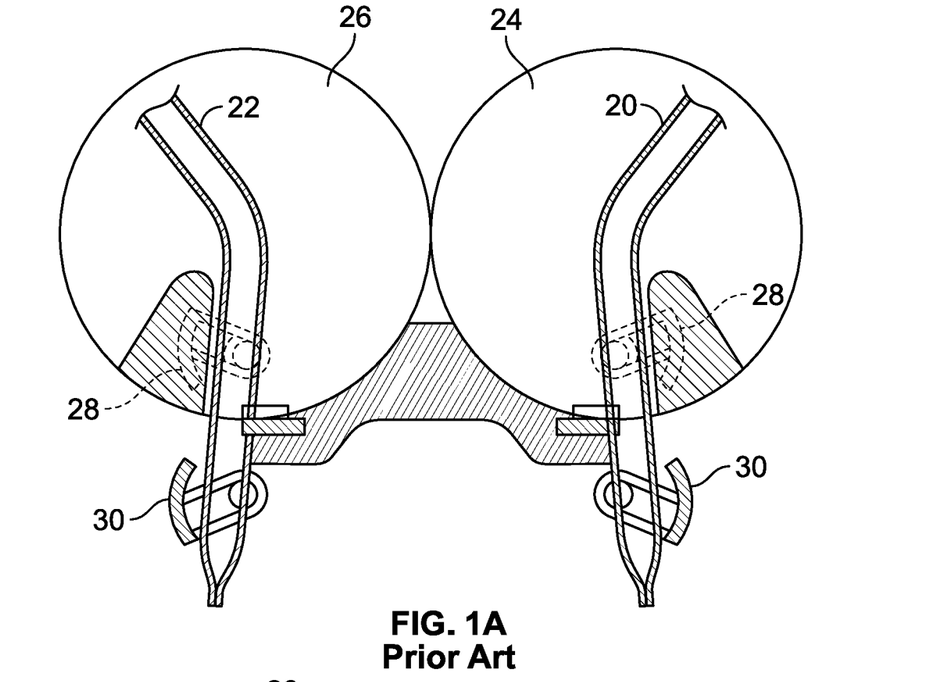
FIGS. 1A-1C show, for background purposes, an embodiment of the device and method for forming a heat-bonded connection described in U.S. Pat. No. 10,040,247, cited above and which is incorporated herein by reference.
Figure 1B:
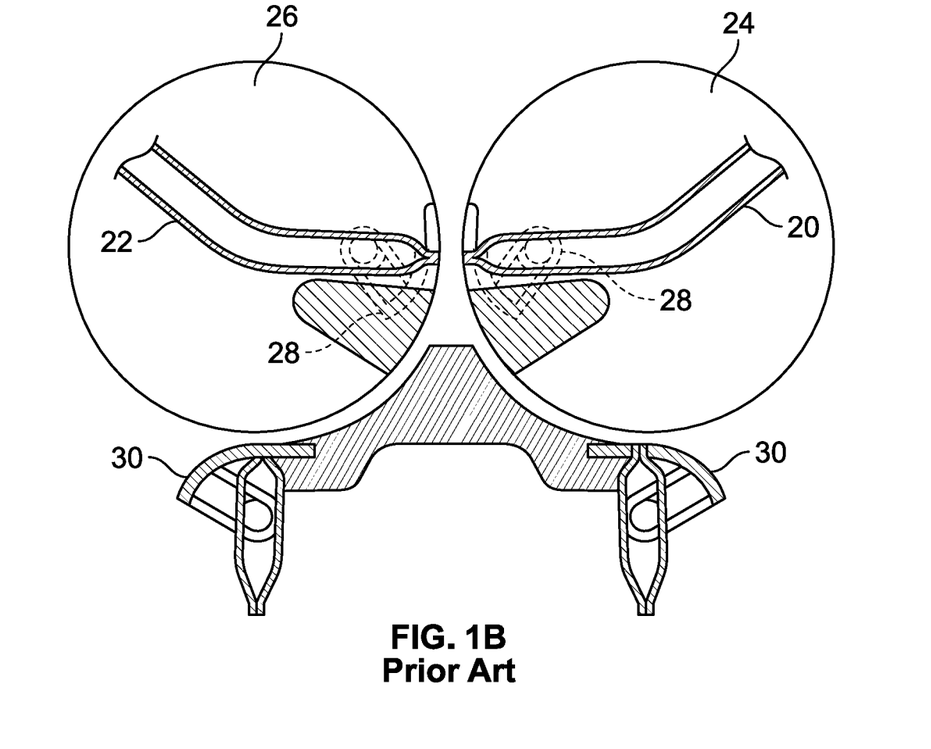
Figure 1C:
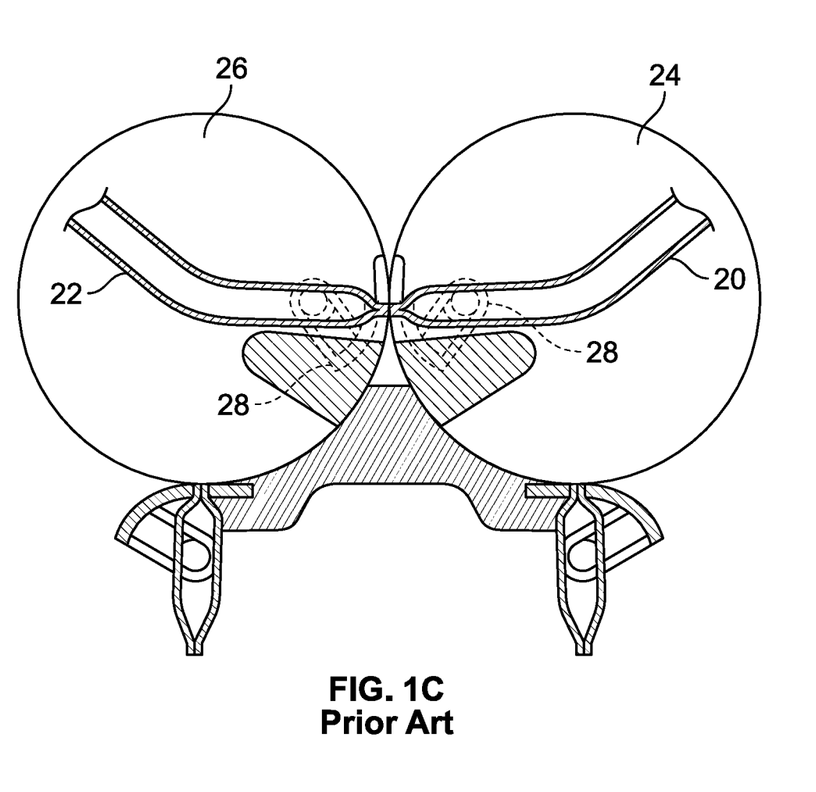

FIGS. 1A-1C are taken from U.S. Pat. No. 10,040,247, and illustrate, for background and description purposes, one example of a prior device and method for forming a heat-bonded (also referred to interchangeably as "melt-bonded" or "welded") connection between two flexible thermoplastic conduits or tubes. Illustration of this particular device does not imply that the present subject matter is useful only with heat or melt bonded connections formed by such device. Connections formed by other apparatuses may also be used with the present subject matter.

Without unduly elaborating on the details of the device and method shown in U.S. Pat. No. 10,040,247, sealed thermoplastic conduit tubing or tubing segments 20 and 22 are each received on a rotatable disc, respectively 24 and 26. Each disc cooperates with two pair of clamping jaws 28 and 30, one of which may also be a high frequency voltage electrode for heating the clamped tubing. As seen in FIG. 1B, after the tubing segments are clamped and heated, the discs shift laterally to separate the clamping jaws and rotate to the positions seen in FIG. 1B. This exerts a tensile and shear force on the tubing segments, such that each tubing segment is separated from the sealed end portion of that segment. Because the clamping jaws 28 keep the ends of the segments clamped and sealed, sterility of the segments, if pre-sterilized, is maintained and, in any event, the tubing segments are safeguarded from introduction of ambient bacteria or microorganisms.

After the tubing segment ends are brought into a facing position by rotation of the discs, as shown in FIG. 1B, the discs move laterally again, bringing the tubing segment ends into direct contact, as seen in FIG. 1C. Because this happens while the tubing ends are still at elevated temperature and in semi-molten state, they form an integral, welded bond or heat-bonded connection site (better seen as connection site 84 in FIGS. 2A, 2B, 3A and 3B).

Because the process may result in a thermoplastic portion or "skin" blocking communication between the lumen of the joined conduits or tubes (see FIGS. 2A, 2B, 3A and 3B), after cooling, manual manipulation may be employed to break the skin and open the connection between the tubing segments for fluid flow. The present subject matter, as described below, avoids the need for manual manipulation.

The tubing or tubing segments 66 and 68, and the connection site 84 are shown more fully in FIGS. 2A-3B. For purposes of describing the connection site opening method and apparatus herein, reference may be made to the longitudinal axis 88, shown in FIGS. 2A and 2B, that extends axially through the lumen or bore of tubing segments 66 and 68 and passes through the seal line 85 at the connection site 84. This axis will be referred to as the connection site axis.

Figure 3A:
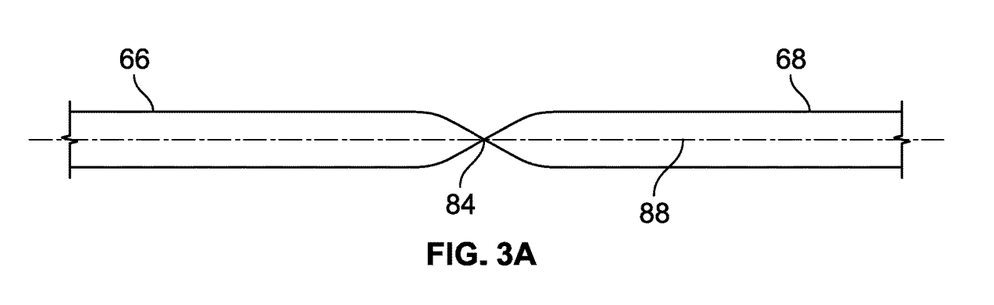
FIGS. 3A and 3B are, respectively, diagrammatic line drawings of the tubing segments of FIGS. 2A and 2B and are employed in later figures to illustrate the structure and function of apparatus and method described herein for disrupting the web or skin blocking fluid flow through the connection site after welding of the tubing or tubing segments together and opening the fluid flow lumen therethrough.
Figure 3B:
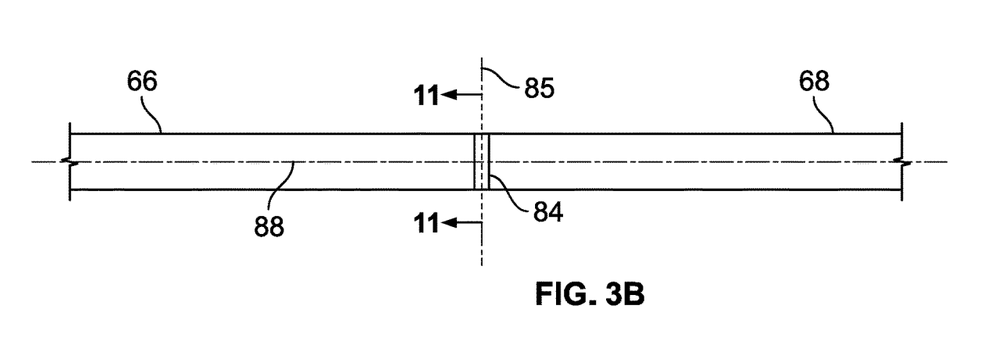
Figure 4:
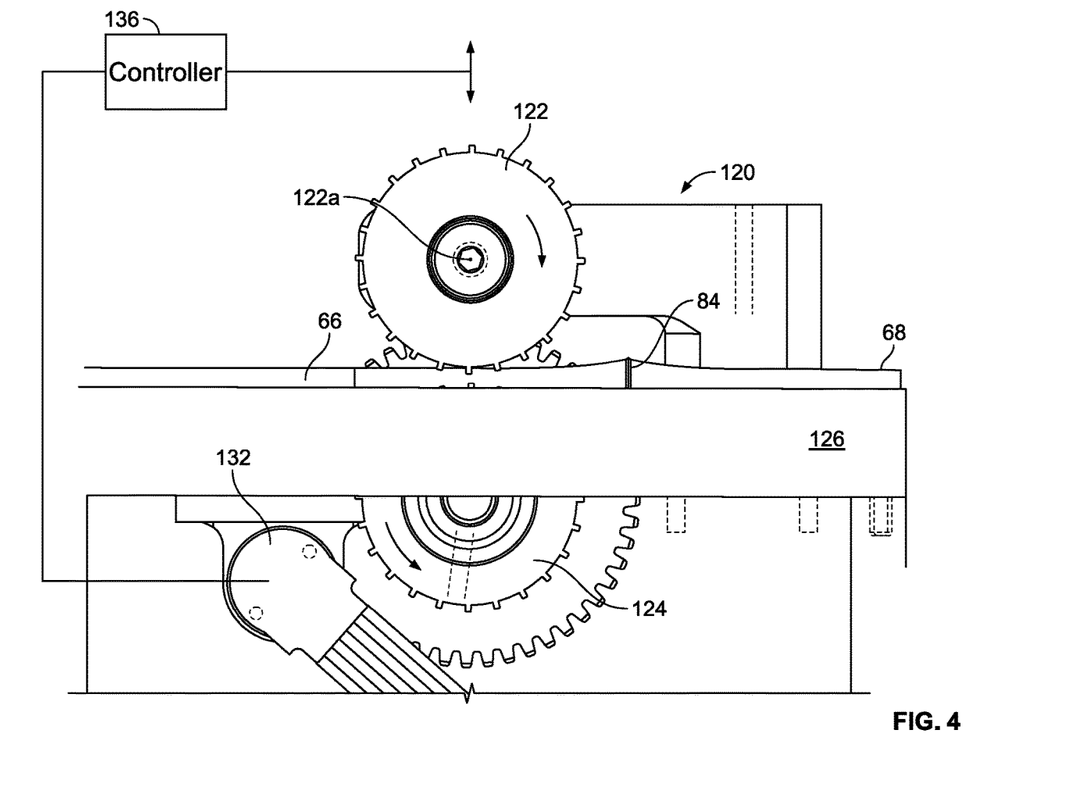
FIG. 4 is a side view of a system for the automated opening of a sterile tubing weld utilizing a pair of rollers.
Figure 5:
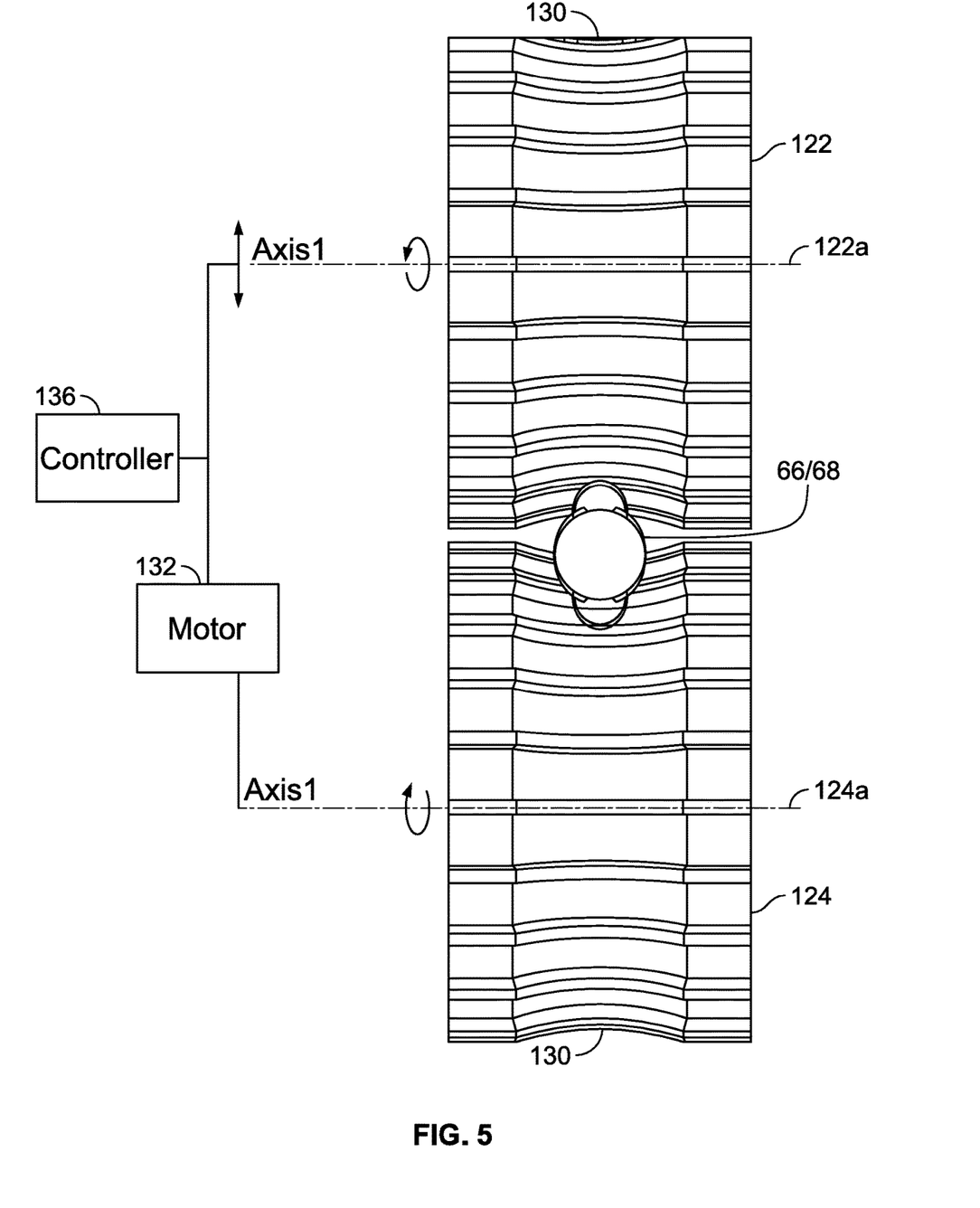
FIG. 5 is view of the rollers of the embodiment of FIG. 4 in which the rollers have a concave surface.
Figure 6:
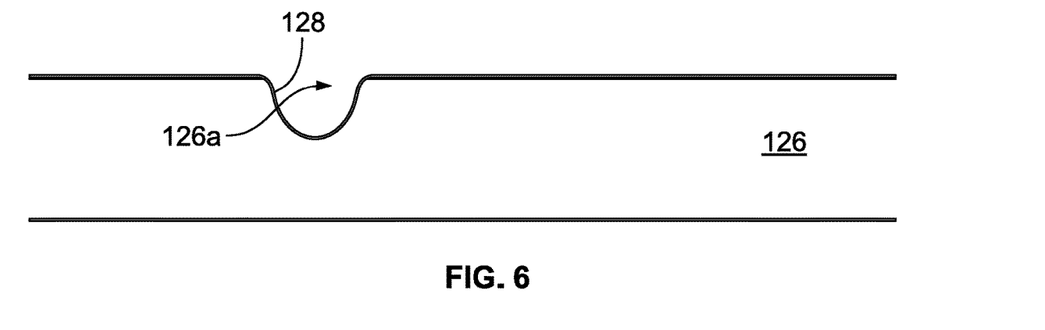
FIG. 6 is an end view of the support surface of the embodiment of FIG. 4 showing an elongated groove aligned with the longitudinal axis of the support surface.

When the heat bonded or welded connection site is formed, associated clamps typically compress or clamp the tubing segments in proximity to the connection site, resulting in a physical appearance of the connected tubing segments 66 and 68 as seen in FIGS. 3A and 3B, wherein the connection site, before opening, extends along a line 85 that may be transverse or orthogonal to the connection site axis 88. FIG. 3A shows the compressed tubing segments 66 and 68 when looking at an end edge of the connection site line. FIG. 3B is from a viewing angle 90 degrees from the viewing angle of FIG. 3A and shows the connection site line 85 along its length, and the outward flaring of the tubing segments at the connection site as a result of the jaws that clamp the tubing during the formation of the connection site. Because of the connection forming process the compressed walls of the tubing segments tend to stick together along the connection or bonding site line 85, thus blocking or reducing flow between the tubing segments.

Figure 2A:
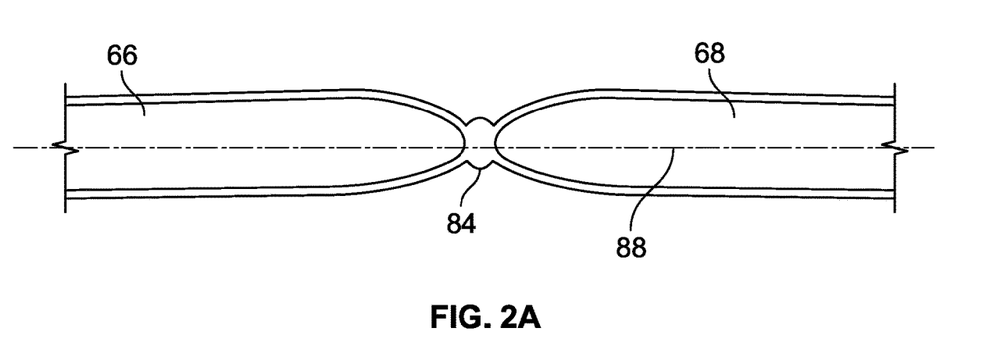
FIGS. 2A and 2B are views, taken at different angles, of two thermoplastic tubes or tubing segments heat bonded or welded together by apparatus and method similar to that shown in FIGS. 1A-1C. For consistent reference purposes only.
Figure 2B:
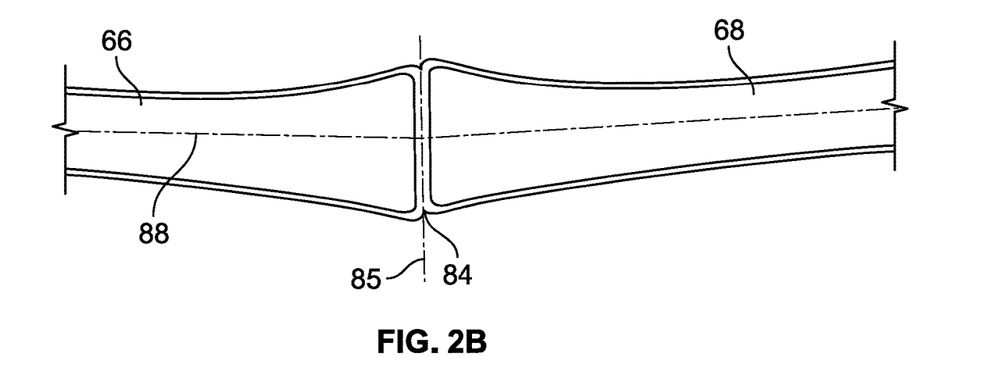

FIGS. 3A and 3B show the tubing segments 66 and 68 and connection site 84 of FIGS. 2A and 2B diagrammatically as line drawings and will be employed in the discussion below to better illustrate the opening apparatus and method. Further, for consistent reference purposes, FIGS. 2A and 3A view the connection site seal line 85 from an end or edge view and are referred to as the top view, while FIGS. 2B and 3B show the length of the connection site seal line 85 and are referred to as the side view. It is thus apparent that the top and side views are taken orthogonally, at 90 degrees, relative to one another.

The closed sterile weld site is commonly opened manually by a user pinching the weld site between his/her fingers and rolling the tube about its axis. Since the closed weld is not cylindrically axisymmetric the pinching force must be applied in a specific direction in order to separate the opposite tubing walls stuck together. To successfully open the weld, the pinching force must be applied parallel to the closed weld line. The tubing walls joined together along the closed bond line will move perpendicular to the direction of the force, causing the walls to separate and the bond site to open. If the force were to be applied perpendicular to the closed weld line, the force would act to further push the joined walls together and the site will not open. Once the sterile weld is pinched open, the tubing's cylindrical symmetry is restored, and the weld is inspected visually by the user.

With reference to FIGS. 4-8, a system 120 for automatically opening a connection site between conjoined tubing segments of a medical fluid path is shown. The system comprises two spaced-apart rollers 122, 124, each rotatable in opposite directions about its respective axis of rotation 122a, 124a, with the axes of rotation 122a, 124a being generally parallel to each other.

The rollers 122, 124 are positioned on opposite sides of a support surface 126 that supports the conjoined tubing segments 66, 68, so that the longitudinal axis 88 of conjoined tubing segments is generally perpendicular to the axes of rotation 122a, 124a of the rollers 122, 124, and in alignment with an axis 126a of the support surface 126. To this end, the support surface 126 may include an elongated groove 128 (best seen in FIG. 6) as a guide for maintaining the conjoined tubing segments 66, 68 in proper alignment with the rollers 122, 124.

To open the connection site, the conjoined tubing segments are placed between the rollers 122, 124 with the connection site axis generally perpendicular to the support surface 126. The rollers 122, 124 engage the conjoined tubing segments and are rotated to draw the connection site into the space between the surfaces of the rollers 122, 124 to compress the connection site with a sufficient force to open it.

Accordingly, at least one of the first and second rollers 122, 124 is moveable relative to the other to provide a space between the rollers sufficiently large to locate the conjoined tubing segment therebetween. A separate actuator may be provided for this purpose. After the conjoined tubing segments are properly positioned between the rollers, the rollers are brought closer together so that a force is exerted on the tubing segments sufficient to open the connection site.

Figure 7:
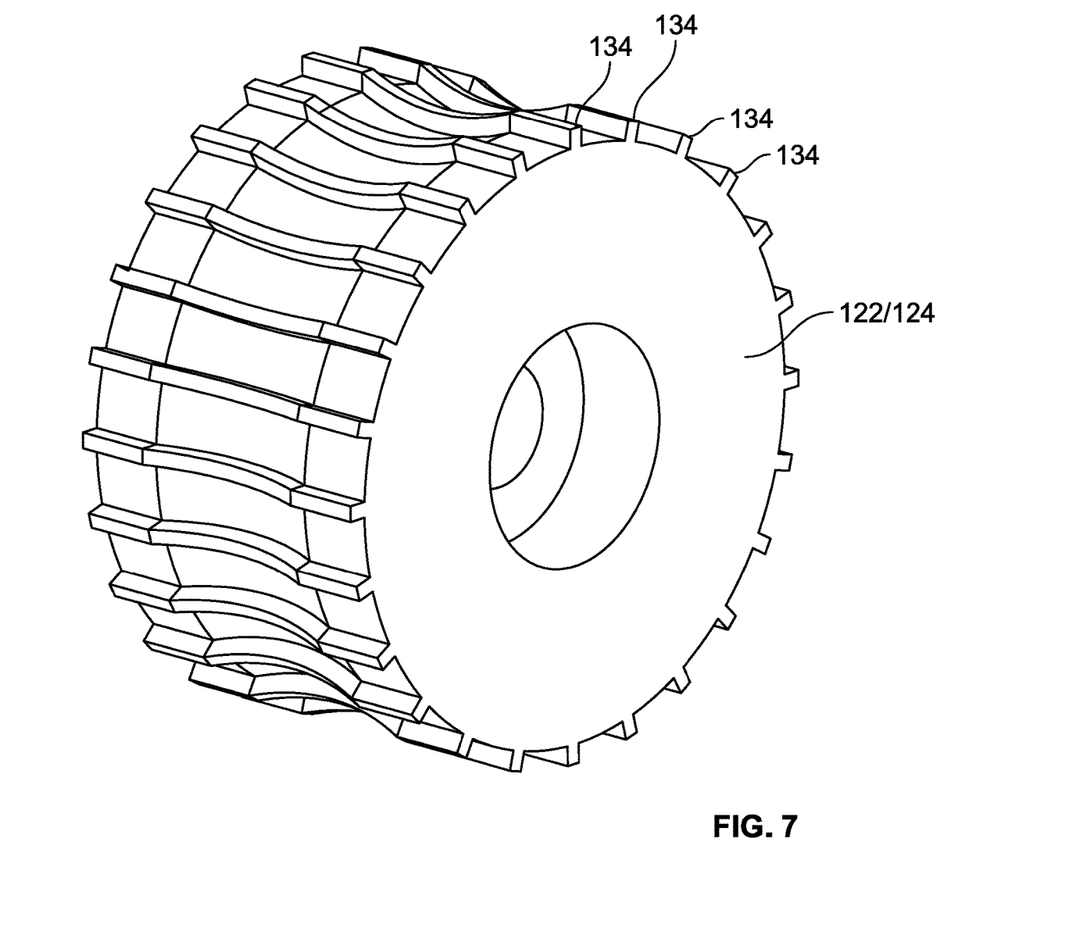
FIG. 7 is a perspective view of a roller of the embodiment of FIG. 4 in which the roller has a series of ridges formed thereon.

At least one of the rollers 122, 124 is provided with a drive motor 132 for imparting rotational motion to the roller. As illustrated, roller 124 is provided with a drive motor 132. Rotation is imparted to the roller 122 by rotation of the roller 124 in engagement with the tubing segments. Alternatively, both rollers 122, 124 can be driven by a drive motor. Further, one or both of the rollers 122, 124 may be provided with a textured surface to increase the traction between the roller and the tubing segments. With reference to FIG. 7, the textured surface may be provided by a series of grooves or ridges 134 formed on the surface of the roller in alignment with the axis of rotation of the roller. Preferably, if only one roller is to be provided with a textured surface, it is a driven roller.

For effective opening of the sterile weld, proper positioning of the welded tubing segment is required such that the weld line axis 84 is oriented generally perpendicular to the axes of rotation 122a, 124a of the rollers 122, 124, with the weld line axis 84 lying in a plane defined by the axes of rotation. If the opening system is incorporated into the sterile weld device, this can be incorporated into the weld process itself, with the way in which the tubing segments are cut and brought together forces the weld line axis to line up with the appropriate orientation. If the opening system is employed separately from the sterile weld device, the opening system is preferably configured to force the tube to be loaded in a way that aligns the tube weld line axis generally perpendicular to the axes of rotation 122a, 124a of the rollers 122, 124.

Figure 8:
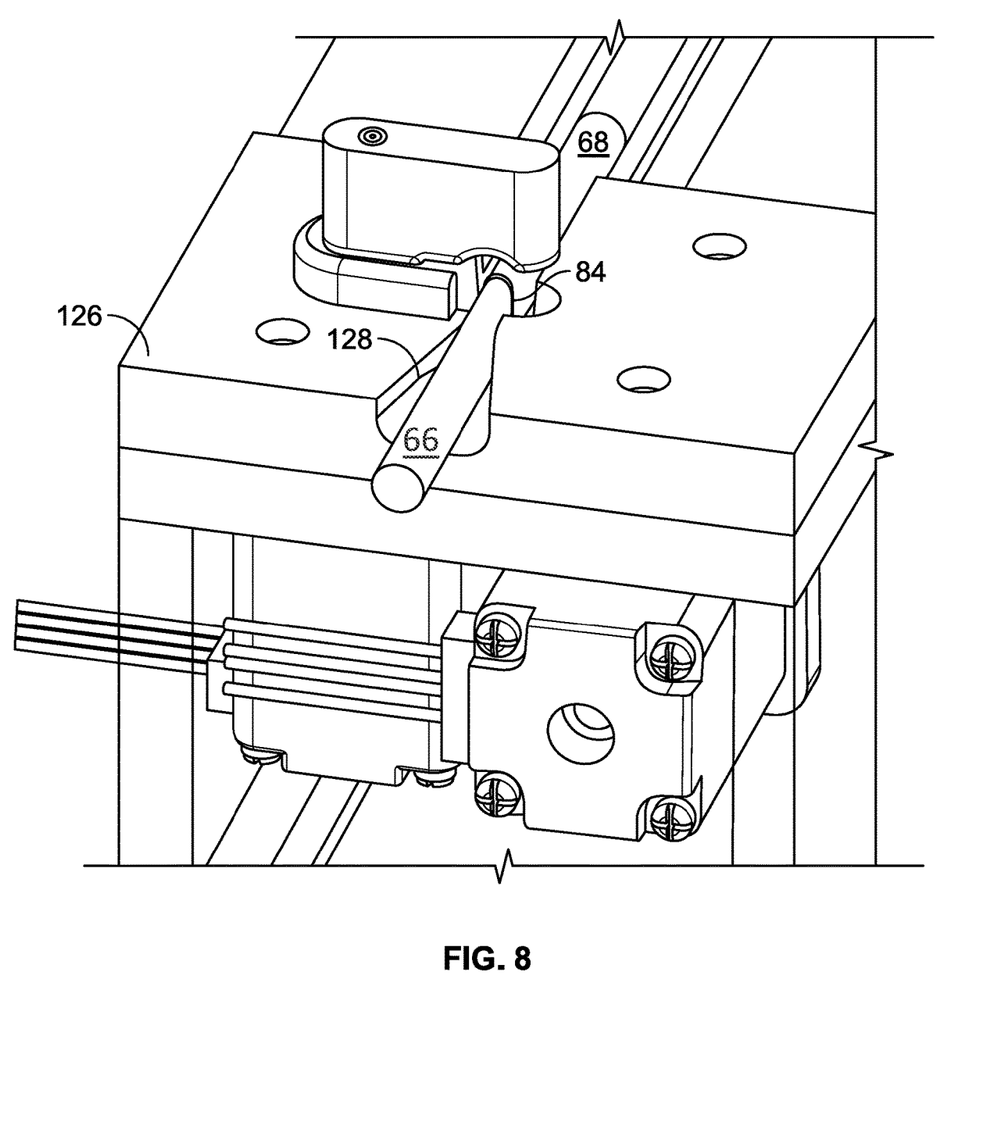
FIG. 8 is a perspective view of a guide configuration that rotates the weld line of a conjoined tubing segment into the proper orientation with respect to the surface of the rollers for opening.

With reference to FIG. 8, one embodiment of a guide 128 is seen in which the entrance to the guide 128 has a funnel or tapered shape that is sufficiently wide at its opening to accommodate the conjoined tubing segments 66, 68 regardless of the orientation of the connection site 84. As shown, the major or weld axis 85 of the connection site 84 is oriented so that the weld axis 85 is substantially horizontal. The width of the guide 128 then narrows so that, as the conjoined tubing segments are drawn through the rollers 122, 124, the side walls of the groove engage the connection site 84, and the conjoined tubing segments are rotated so that the weld axis 85 is substantially vertical and perpendicular to the surfaces of the rollers 122, 124. As can be appreciated, the support surface 126 may be provided with other structures, such as raised surfaces, to act as a guide to maintain the tubing segments in proper alignment with the rollers. In addition, the rollers 122, 124 may be provided with a concave surface 130 (best seen in FIG. 5) that also helps to maintain the longitudinal axis 88 of tubing segments 66/68 aligned with the axis 126a of the support surface 126.

Preferably, a programmable controller 136 is provided that controls the system to automatically space the first and second rollers 122, 124 apart a distance sufficient to receive the conjoined tubing segments therebetween. Then, the controller 134 causes the conjoined tubing segments to be positioned between the first and second rollers, with the longitudinal axis 88 of the conjoined tubing segments generally perpendicular to the axes of rotation 122a, 124a of the rollers 122, 124, and in alignment with an axis 126a of the support surface 126. The controller 134 then causes one or both of the first and second rollers to move into engagement with the conjoined tubing segments and activates the drive motor to rotate the rollers so as to draw the connection site of the tubing segments between the rollers, where a compressive force is exerted on the connection site sufficient to open the connection site. Once the flow path through the connection site is opened, the controller stops the drive motor and causes one or both of the first and second rollers to move out of engagement with the connection site at a distance sufficient to permit removal of the conjoined tubing segments from between the rollers.

Thus, systems and methods have been provided that use rotatable rollers to automatically break or otherwise disrupt the thermoplastic skin or web and therefore more fully open such a connection site and the lumen of the tubing segments to allow or improve fluid flow between the connected tubing segments. It will be understood that the embodiments described above are illustrative of some of the applications of the principles of the present subject matter. Numerous modifications may be made by those skilled in the art without departing from the spirit and scope of the claimed subject matter, including combinations of features that are individually disclosed or claimed herein.

The invention claimed is:

1. A system for automatically opening a heat bonded connection site between two conjoined tubing segments of a medical fluid path, the conjoined tubing segments defining a longitudinal axis and the connection site defining a seal line axis generally perpendicular to the longitudinal axis of the conjoined tubing segments, the system comprising:
  a) a support surface defining a horizontal plane and having a first axis for receiving the conjoined tubing segments with the longitudinal axis of the conjoined tubing segments in alignment with the first axis of the support surface;
  b) first and second spaced-apart rollers, each rotatable about a horizontal axis generally perpendicular to the first axis of the support surface, wherein a portion of the support surface is positioned between the first roller and the second roller, with the first roller being positioned above said portion of the support surface and the second roller being positioned below said portion of the support surface so that the conjoined tubing segments are positioned between the first and second rollers when the conjoined tubing segments are positioned on the support surface with the longitudinal axis in alignment with the first axis, at least one of the first and second rollers being movable toward and away from the other one of the first and second rollers; and
  c) a drive motor associated with at least one of the first and second rollers for rotating said at least one of the first and second rollers about its axis, wherein
    an upstream portion of the support surface defines a guide extending from an entrance to an exit,
    a width of the guide at the entrance is sufficiently wide so as to accommodate the conjoined tubing segments regardless of the orientation of the connection site,
    the width of the guide at the exit is sufficiently narrow so as to accommodate the conjoined tubing segments only when the seal line axis is substantially vertical, and
    the width of the guide decreases from the entrance to the exit so as to cause the connection site to be rotated into an orientation in which the seal line axis is substantially vertical as the conjoined tubing segments are drawn from the entrance to the exit; and
  d) a controller for automatically operating the system to bring the first and second rollers into engagement with the conjoined tubing segments, to rotate the first and second rollers to draw the connection site of the conjoined tubing segments therebetween and to exert a compressive force on the connection site sufficient to open a flow path between the conjoined tubing segments, and to space the first and second rollers apart a distance sufficient to permit removal of the conjoined tubing segments from between the first and second rollers.

2. The system of claim 1 wherein at least one of the first and second rollers has a concave surface.

3. The system of claim 1 wherein at least one of the first and second rollers has a textured surface.

4. The system of claim 3 wherein the textured surface comprises a series of ridges formed on the surface of said at least one of the first and second rollers, the ridges extending in a direction generally parallel to the axis of rotation of said at least one of the first and second rollers.

5. The system of claim 1 wherein the guide is defined by an elongated groove of the support surface in alignment with the first axis of the support surface.

6. The system of claim 1, wherein the guide has a tapered shape.

7. The system of claim 1 wherein the support surface has at least one raised surface configured to maintain the conjoined tubing segments in proper alignment with the first and second rollers.

8. A controller-implemented method for opening a heat-bonded connection site between two conjoined tubing segments of a medical fluid path positioned on a support surface defining a horizontal plane, with at least a portion of the support surface being positioned between a first roller positioned above the conjoined tubing segments and a second roller positioned below the conjoined tubing segments, with the conjoined tubing segments defining a longitudinal axis in alignment with a first axis of the support surface, and with the connection site defining a seal line axis generally perpendicular to the longitudinal axis of the conjoined tubing segments, the method comprising:
  a) bringing the first and second rollers into contact with the conjoined tubing segments;
  b) rotating the first and second rollers about horizontal axes to draw the connection site of the conjoined tubing segments between the first and second rollers so as to exert a pressure on the connection site sufficient to open a flow path between the conjoined tubing segments; and
  c) stopping rotation of the first and second rollers and moving the first and second rollers apart a distance sufficient to permit removal of the conjoined tubing segments from between the first and second rollers, wherein
    an upstream portion of the support surface defines a guide extending from an entrance to an exit,
    a width of the guide at the entrance is sufficiently wide so as to accommodate the conjoined tubing segments regardless of the orientation of the connection site,
    the width of the guide at the exit is sufficiently narrow so as to accommodate the conjoined tubing segments only when the seal line axis is substantially vertical, and
    the width of the guide decreases from the entrance to the exit so as to cause the connection site to be rotated into an orientation in which the seal line axis is substantially vertical as the conjoined tubing segments are drawn from the entrance to the exit.

9. The method of claim 8 wherein at least one of the first and second rollers has a concave surface.

10. The method of claim 8 wherein at least one of the first and second rollers has a textured surface.

11. The method of claim 10 wherein the textured surface comprises a series of ridges formed on the surface of said at least one of the first and second rollers, the ridges extending in a direction generally parallel to the axis of rotation of said at least one of the first and second rollers.

12. The method of claim 8 wherein the support surface includes at least one raised surface configured to maintain the conjoined tubing segments in proper alignment with the first and second rollers.

13. The method of claim 8 wherein the guide is defined by an elongated groove of the support surface in alignment with the first axis of the support surface.

14. The method of claim 8 further comprising aligning the seal line axis of the conjoined tubing segments relative to the first and second rollers by drawing the conjoined tubing segments through the guide.

15. The method of claim 8 wherein the guide has a tapered shape.

16. The method of claim 8, automatically executed by a programmable controller.

17. The system of claim 1, wherein the guide has a funnel shape.

18. The method of claim 8, wherein the guide has a funnel shape.

* * * * *